United States Patent
Taub et al.

(10) Patent No.: US 7,147,464 B2
(45) Date of Patent: *Dec. 12, 2006

(54) PLACING AN ORTHODONTIC ELEMENT ON A TOOTH SURFACE

(75) Inventors: Eldad Taub, Reut (IL); Baruch Nissenbaum, Ramat Gan (IL); Avi Kopelman, Ramat-Chen (IL)

(73) Assignee: Cadent Ltd, Or Yehuda (IL)

( * ) Notice: Subject to any disclaimer, the term of this patent is extended or adjusted under 35 U.S.C. 154(b) by 37 days.

This patent is subject to a terminal disclaimer.

(21) Appl. No.: 10/914,287

(22) Filed: Aug. 10, 2004

(65) Prior Publication Data

US 2005/0095551 A1  May 5, 2005

Related U.S. Application Data

(60) Continuation of application No. 10/752,410, filed on Jan. 7, 2004, now Pat. No. 6,976,840, which is a division of application No. 09/940,742, filed on Aug. 28, 2001, now Pat. No. 6,695,613, which is a division of application No. 09/536,934, filed on Mar. 27, 2000, now Pat. No. 6,334,772, which is a continuation of application No. PCT/IL98/00451, filed on Sep. 17, 1998.

(30) Foreign Application Priority Data

Sep. 30, 1997 (IL) ..................................... 121872

(51) Int. Cl.
*A61C 3/00* (2006.01)
(52) U.S. Cl. ............................................. 433/24; 433/3
(58) Field of Classification Search ................. 433/2–4, 433/8, 24, 29, 75
See application file for complete search history.

(56) References Cited

U.S. PATENT DOCUMENTS

| 4,850,864 | A | 7/1989 | Diamond |
| 5,290,168 | A | 3/1994 | Cooper |
| 5,294,792 | A | 3/1994 | Lewis et al. |
| 5,448,472 | A | 9/1995 | Mushabac |
| 5,587,284 | A | 12/1996 | Brattesani |
| 5,774,602 | A | 6/1998 | Taguchi et al. |
| 6,123,544 | A | 9/2000 | Cleary |

FOREIGN PATENT DOCUMENTS

| FR | 2655838 | 6/1991 |
| FR | 2656215 | 6/1991 |
| WO | WO 90/08512 | 9/1990 |
| WO | WO 94/24957 | 11/1994 |
| WO | WO 97/03622 | 2/1997 |

*Primary Examiner*—John J Wilson
(74) *Attorney, Agent, or Firm*—Nath & Associates PLLC; Gregory B. Kang; Derek Richmond

(57) ABSTRACT

A method for for comparing between an orthodontic element's actual position on the surface of a tooth and a proper position comprise monitoring the element, the tooth or both once the element and the tooth are proximal to one another by an image acquisition unit which transmits an image to a screen that displays the image and displaying information on the screen regarding proper position of the element in a manner allowing to compare between the actual and the proper position is disclosed.

Further disclosed is a system and device for positioning of an orthodontic element or a marking device having a marking member for marking a position for subsequent placement of an orthodontic element on a surface of a tooth.

17 Claims, 7 Drawing Sheets

PLACING AN ORTHODONTIC ELEMENT ON A TOOTH SURFACE

This is a continuation application of U.S. patent application Ser. No. 10/752,410 filed Jan. 7, 2004; now U.S. Pat. No. 6,976,840, which is a divisional application of U.S. patent application Ser. No. 09/940,742 filed Aug. 28, 2001; now U.S. Pat. No. 6,695,613, which is a divisional of U.S. patent application Ser. No. 09/536,934 filed Mar. 27, 2000 now U.S. Pat. No. 6,334,772 which is a continuation of international patent application PCT/IL98/00451 with an international filing date of Sep. 17, 1998.

FIELD AND BACKGROUND OF THE INVENTION

The present invention is generally in the field of orthodontics and provides a method, system and device for placing an orthodontic element e.g. a bracket on the surface of a tooth of an individual undergoing orthodontic treatment or for marking the spot on a tooth where such an element should be placed.

One of the most critical steps in an orthodontic treatment is the proper placement of brackets on surfaces of teeth of treated individuals. The location of the bracket on the tooth as well as its orientation is a critical factor in determining the direction of movement of the teeth during the treatment. In current orthodontic practice, the orthodontist decides on a general scheme of placing the brackets on the teeth and then attaches each of them to the surface of a tooth, in an exact location and orientation decided at the time of such placing. Preparatory to an orthodontic treatment, the orthodontist typically prepares a plaster model of the teeth of the treated individual and on the basis of such model, the general scheme of placement of the brackets can be decided. However, there is currently no available method which will allow to position the bracket correctly on a tooth surface, based on a determination made previously, e.g. based on a model.

In orthodontic treatment, the brackets are typically placed on the buccal surface of the teeth. At times, it is desired both from a treatment perspective as well as for reasons of external appearance of the individual, to place the brackets on the lingual surface of the teeth. However, by current methods it is difficult to properly position the brackets on the lingual surfaces, particularly in view of difficulties in monitoring the position during attachment of the brackets.

GENERAL DESCRIPTION OF THE INVENTION

It is an object of the present invention to provide a method, system and device for positioning of an orthodontic element on a surface of a tooth, or for marking the position, where an element has to be subsequently placed. The positioning may be based on a prior determination of the proper position of the element on a tooth.

The term "position" is used herein to denote either the element's location on the surface of a tooth, its orientation or a combination of location and orientation. The term "positioning" will be used to denote the act of placing the bracket on the surface of a tooth in a desired position. The term "element" is used herein to denote a device, which is fixed on to a tooth within the framework of an orthodontic treatment, e.g. a bracket.

In accordance with one aspect of the invention, there is provided a method for positioning and fixing an orthodontic element on a surface of a tooth, comprising:

(a) bringing the element into proximity of the tooth while continuously capturing an image of at least the tooth or of the element; and an image of both, once the tooth and the element are proximal to one another;
(b) transmitting the image or its representation to a display for displaying a real-life image of the captured image or representation together with indicators providing guidance information on intended position of the orthodontic element on the tooth's surface;
(c) positioning the element on a tooth's surface according to said indicators such that the element's position coincides with the intended position; and
(d) fixing the element onto the tooth.

In accordance with another aspect of the invention there is provided a method for marking an intended position on a tooth where an orthodontic element is to be placed and fixed, the method comprising:

(a) providing a marking device with a marking member for making a visible mark on a tooth's surface;
(b) manipulating said device so as to bring said member into proximity of the tooth's surface while continuously capturing an image of at least the tooth or of the marking member, and of both once the tooth and the marking member are proximal to one another;
(c) transmitting the image or a representation thereof to a display displaying said image or representation together with indicators providing guidance information on the intended position of the orthodontic element;
(d) fixing the position of the marking member on the tooth's surface according to said indicators, such that the marking member's position coincides with the intended position of the orthodontic element; and
(e) applying a mark on the tooth's surface at said position.

The marking device may be a device adapted to attach a sticker to mark the position where the orthodontic element is to be fixed; adapted to make a color mark on the tooth, e.g. by stamping, so as to mark said position; etc. The marked position of the element can then serve as guidance for replacement of an orthodontic element on the surface of a tooth.

In the following description the captured image or its representation which is displayed on the screen will be referred to at times as "real-life image". As will be explained further below, coincidental with the real-life image, the display may also show a "virtual image" of the same object (the orthodontic element or one or more teeth) seen in the real-life image.

The indicators providing the guidance information on the screen may be represented in a number of ways. For example, the indicators may consist of a display of vectors defining the direction for s change of position or of a change of orientation needed in order to yield a position of the element on a surface of a tooth which was determined to be that which will yield optimal results in the orthodontic treatment (such position will also be referred to herein at times as "proper position"). By another example, the guidance information may be provided in the form of a target sign, e.g. an "×" or a "+" marking the point of proper position of the orthodontic element superimposed on a display real-life image. By a further example, the guidance information may be provided as a virtual image of objects corresponding to those of the real-life image, e.g. a graphic representation of boundaries of objects in the image (of the teeth or of the orthodontic element) which are presented such that once the real-life objects are made to overlap the responding object of the virtual image, proper position is attained. As will be understood the above are mere examples and a variety of other graphic representations providing guidance information may also be used.

The real-life image and the guidance information are superimposed together on display. In order to yield a proper position of the orthodontic treatment, the element is moved or rotated, based on the guidance information, until its real-life image displayed on the screen yields a correct position as determined on the basis of the indicators on the screen. For example, the proper position of an orthodontic bracket may be represented as a virtual image, e.g. boundaries of a bracket, superimposed on the real-life image of a tooth on which the bracket is to be fixed, and the bracket may then be manipulated until the boundaries of its real-life image overlap those of the virtual image. Alternatively, the real-life image may be centered on the orthodontic element, e.g. the bracket, such that the orthodontic element is always in a fixed position on the screen. In such latter case, a virtual image of at least one tooth may be displayed and the bracket may then be repositioned and/or rotated until the at least one tooth of the real-life image overlaps that of the virtual image, thus attaining the proper position.

By a further alternative, the displayed guidance information indicators, consist of a virtual image of both at least one tooth and of the orthodontic element in a proper position of the latter. The user may then first be required to adjust the image capturing unit such that the displayed virtual image of the at least one tooth will overlap the corresponding at least one tooth of the real-life image, and then manipulate the orthodontic element until its position coincides with that of the virtual image.

The same above alternatives apply also, *mutatis mutandis*, in the case of the method defined above for making an intended position of an orthodontic element on a tooth.

A preferred embodiment of the invention, which will be illustrated in more detail below, concerns the case where the real-life image centers on the orthodontic element or the marking member, in which case the real-life image thereof is continuously displayed in a fixed position of the display. A particularly preferred embodiment of the invention is such where the image capturing unit is mounted on the positioning device of the orthodontic element or of the marking member, thus having the orthodontic element or the marking member (as the case may be) in a fixed position of its field of view. It should however be noted that it is possible also to achieve the same effect namely displaying the real-life image of the orthodontic element on the display in a fixed position and orientation, by other means: for example, a stationary image capturing unit having the element in its field of view captures the image of the orthodontic element or the marking member and then by various rapid (real-time) image processing algorithms the orthodontic element or the marking member may always appears in defined spot of the display. For this purpose the image processing software may identify the element or the marking member by its contours, by its color or reflectiveness, by other clues, e.g. markings displayed thereon, etc.

The method according to this preferred embodiment for positioning and fixing an element on a surface of a tooth comprises:
(a) mounting the element on a positioning device;
(b) bringing the element into proximity of said surface while continuously monitoring the element by an image acquisition unit which captures an image of the element and its surroundings and transmits this image to a screen;
(c) displaying on the screen
  (i) said image,
  (ii) guidance information relating to a proper position of the element on said surface;
(d) in case of discrepancy between actual position of said element, being the position of the element viewed on the screen, and said proper position, correcting the actual position to match said proper position; and
(e) fixing said element on said surface.

The method according to the preferred embodiment for marking a position on the surface of a tooth where an orthodontic element is to be subsequently positioned, the method comprising:
(a) a marking device, having a marking member for making a visible mark on a tooth;
(b) bringing the marking member into proximity of said surface while continuously monitoring the marking member by an image acquisition unit which captures an image of the marking member and its surrounding and transmits this image to a screen;
(c) displaying on the screen
  (i) said image,
  (ii) guidance information relating to a proper position of the element on said surface;
(d) in case of a discrepancy between actual position of said marking member, being the position viewed on the screen, and said proper position, correcting the actual position to match said proper position; and
(e) marking said position on said surface.

The invention also provides a method for comparing between an orthodontic element's actual position on the surface of a tooth and a proper position, the method comprising:
(a) monitoring the element, the tooth or both once the element and the tooth are proximal to one another by an image acquisition unit which transmits an image to a screen that displays said image;
(b) displaying information on said screen regarding proper position of said element in a manner allowing to compare between the actual and the proper position.

The information on proper position of the element may, for example, be displayed in the form of a virtual image of the tooth on which the element is to be fixed, e.g. in the form of lines tracing the boundaries of the tooth. The virtual image may at times be displayed on the screen superimposed on a displayed real image of the element or the marking member and its surrounding, with the superimposition being such that when the element or the marking member is in its proper position on the tooth, the real image matches the virtual image. Additionally, said information may also be displayed in the form of lines tracing the boundaries of the tooth optionally together with lines tracing boundaries of neighboring teeth. The orthodontist or the technician, which positions and fixes the element or the marking device on to the tooth, manipulates its position until such match is achieved.

Information regarding proper position may be obtained by a variety of methods. For example, it may be obtained on the basis of a virtual three-dimensional computerized model of the teeth, which is then used for a computerized design of the proper position. From such a model a virtual image of the teeth, which is a frontal image at an angle in which the real image of the teeth will subsequently be captured by the image acquisition unit can then be generated. A three-dimensional virtual teeth model may be obtained, for example, in a manner described in PCT Application, Publication No. WO 97/03622 or that described in German Patent Application PCT Application, Publication No. WO 94/24957, the contents of which are being incorporated herein by reference. Additionally, an element's proper position may also be obtained from a treatment scheme planned on the basis of a physical model, e.g. a three-dimensional plaster model. For example, brackets or mock-up brackets may be fixed on such a model within the framework of a treatment design, and then an image of a bracket on such a teeth model may be captured from an angle substantially the same as that of the real image of the teeth which will be captured by the image acquisition unit.

The display screen may typically be a television screen, a computer display, an eyepiece display, (e.g. fixed to the frame attached to the orthodontist's head), and many others.

The present invention also provides a system for positioning an orthodontic element or a marking device having a marking member for marking a position for subsequent placement of an orthodontic element on a surface of a tooth, comprising:

an image acquisition unit for capturing an image of the tooth or of said element, and an image of both once the tooth and said element are proximal to one another;

an image grabber coupled to said image acquisition unit for receiving the image captured by the image acquisition unit and transmitting an image or a representation thereof to a display unit; and a display unit, coupled to the image grabber, for displaying said image or representation.

The system of the invention preferably comprises also a module, coupled to said display unit, for transmitting to the display unit data relating to guidance information relating to correct position of the orthodontic element on the tooth's surface, for display by said display unit in a super-imposed position to the displayed real-life image or representation thereof. The guidance information will typically, but not exclusively, be displayed on the screen as a representation of boundaries of either the orthodontic element or the teeth, which once matched with corresponding boundaries of the displayed real-life image or representation, will yield a proper position. Such a proper position display may for example be an indication, superimposed on the tooth's image, of the correct position of the orthodontic element. Alternatively, such representation may consist of boundaries of teeth superimposed on an image of the orthodontic element (which is maintained in the image in a fixed position) and by moving the orthodontic element and matching the viewed image with the real-life image in a manner that teeth boundaries of both images coincide, correct positioning will be attained. The same applies, *mutatis mutandis*, also for a placing of a member of a marking element.

By preferred embodiment of the above system, the image acquisition unit, typically a small video camera fitted with a lens allowing near focus and a wide field of view is mounted on the positioning device. In such a positioning device the element or the marking device, as the case may be, is typically held in a fixed place, and the image acquisition unit is also fixed on said device such that the image of the element or marking device will always be in a defined place in the captured image.

The invention further provides a positioning device for positioning an orthodontic element on the surface of a tooth, comprising:

a gripping member for holding said element and releasing it once it is fixed on the tooth surface; and an image acquisition unit for capturing an image of the element held on the zipping member and of its surrounding.

The invention still further provides a marking device for marking a position for subsequent placement of an orthodontic element on a surface of a tooth, comprising:

a marking member held on said marking device in a manner allowing to mark said position on a tooth surface; and an image acquisition unit for capturing an image of the marking device and of its surrounding.

The positioning device of the invention allows to position and fix orthodontic elements in a proper position even on surfaces, which are difficult to view. A particular example is placing brackets on lingual surfaces of teeth.

The invention will now be illustrated below by some non-limiting specific embodiments, with references to the figures in the attached drawings. The illustrated embodiments refer to positioning of a bracket, it being understood that the invention applies, *mutatis mutandis* also to positioning of other orthodontic elements.

BRIEF DESCRIPTION OF THE DRAWINGS

FIGS. 4A–4C show the image, which is displayed on the screen, wherein:

FIG. 4A illustrates the real image captured by the video camera;

FIG. 4B illustrates a virtual image on the proper position of the bracket; and

FIG. 4C illustrates a superimposition of the images of FIGS. 4A and 4C.

FIGS. 5A–5B show a real image as captured by the image acquisition unit camera superimposed with a virtual image displayed as lines of teeth boundaries, wherein:

FIG. 5A shows the bracket not in the proper position; and

FIG. 5B shows the bracket in its proper position with the teeth borders matching the contours of the virtual image;

DESCRIPTION OF SPECIFIC EMBODIMENTS

Figure 1:
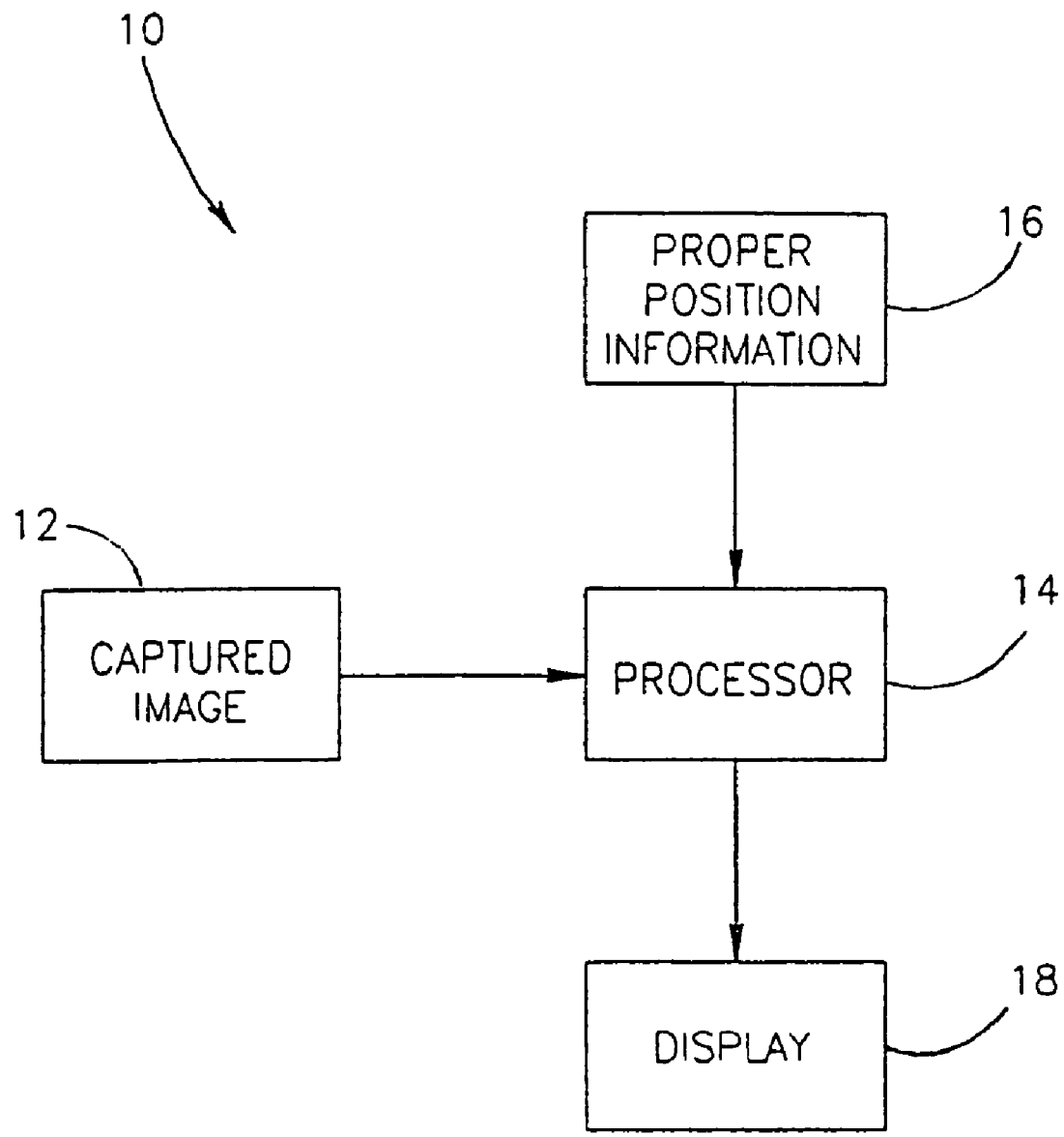
FIG. 1 is a block diagram showing the general design scheme of a system in accordance with the invention.

Reference is first being made to FIG. 1 showing the general scheme of a system 10 in accordance with an embodiment of the invention. An image 12 captured by an image acquisition unit is transmitted comprising the first unit 12 which comprises a camera to a processor 14 which also receives proper position information 16 and transmits both to display screen 16, e.g. a television screen, a computer monitor screen, etc. The image displayed on the screen may be captured by the image ("real life image") and may be an image displaying the proper position information, or a superimposition of both one on the other.

Figure 2:
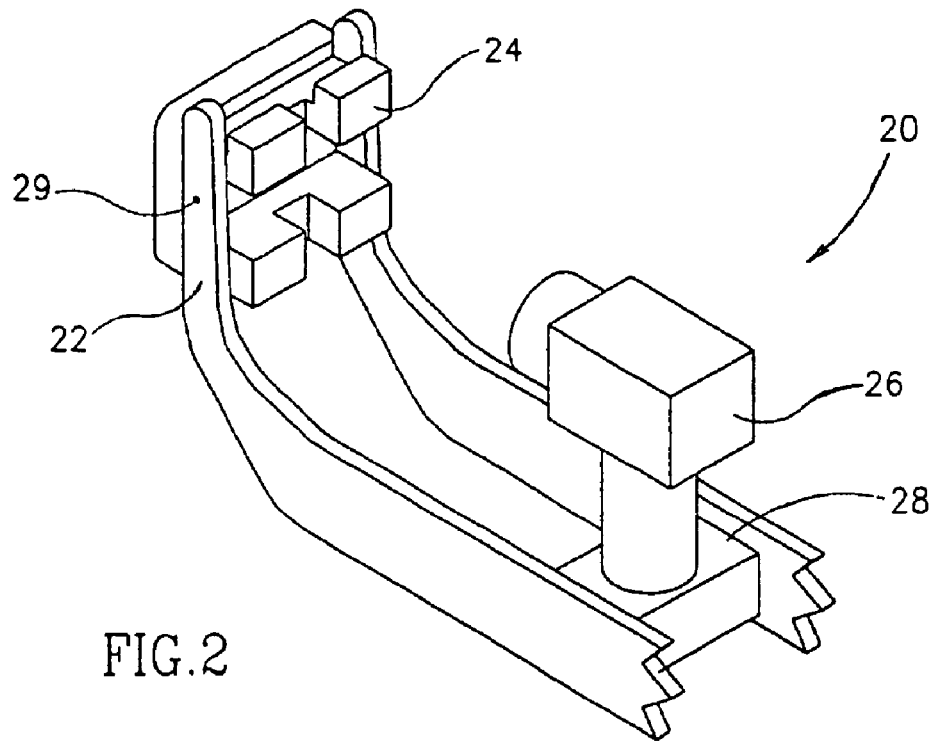
FIG. 2 shows a bracket-positioning device in accordance with an embodiment of the invention.

A bracket-positioning device 20 in accordance with an embodiment of the invention is shown in FIG. 2. This device, of which only the front part is shown (the rear part where the device may be held by the orthodontist is not shown) comprises bracket grippers 22, holding a bracket 24, a video camera 26, mounted on a mount 28 integral with bracket gripper 22. Bracket 24 may be fixed at a determined place in an exact position by means of a removable pin 29. It should be noted that rather than a video camera other image acquisition units may be used, e.g. a CCD device.

Figure 3:
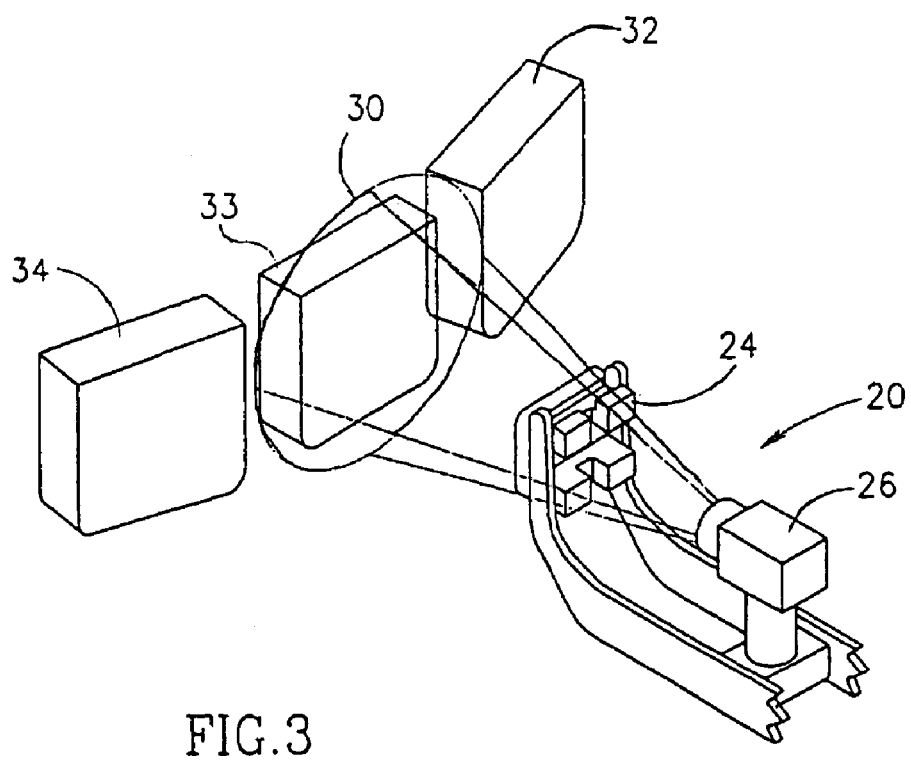
FIG. 3 shows the device of FIG. 2 during the process of positioning the bracket for fixing on a surface of a tooth (the teeth being schematically represented by rectangles), illustrating also the field of view of the camera.

As can be seen in FIG. 3, the video camera 26 is positioned such and has a field of view, represented by a circle 30, allowing to view bracket 24 (typically at the center of the real life image), and tooth 33 on which the bracket is to be fixed, as well as at least a portion of the neighboring teeth 32 and 34. It is to be noted, that for proper positioning, the camera's field of view should be wide enough to show boundaries of the tooth. This may be achieved either by insuring sufficient distance between bracket 24 and video camera 26 or alternatively by fitting camera 26 with a wide-angle lens.

Figure 4A:
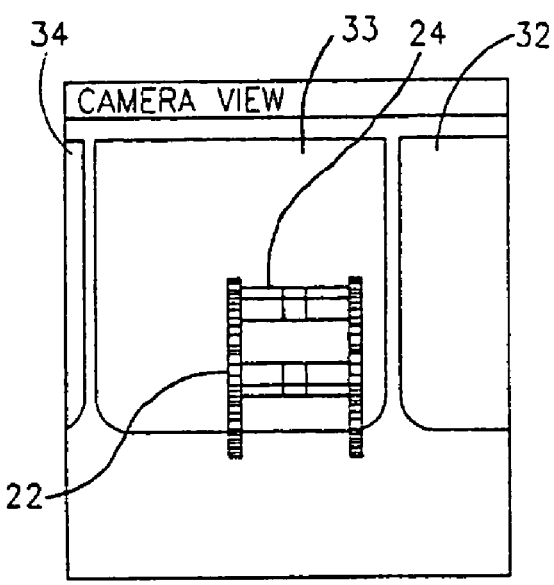
Figure 4B:
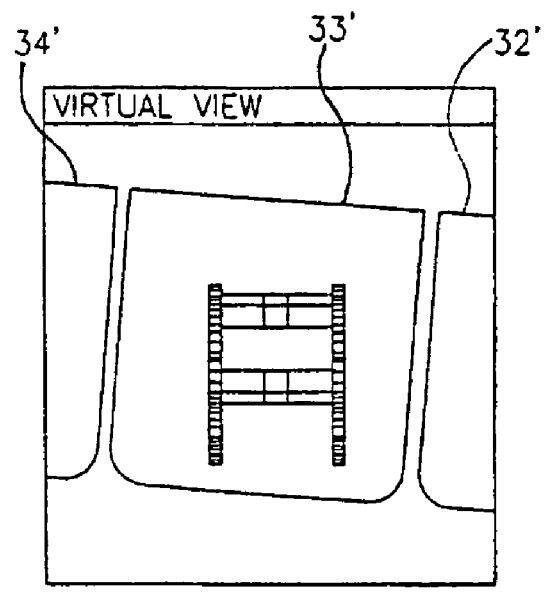

FIG. 4A illustrates schematically a real life image as viewed by camera 26. Seen in FIG. 4A are tooth 33, portions of neighboring teeth 32 and 34 and bracket 24 at the center, held on a bracket gripper 22. A virtual image can be seen in FIG. 4B comprising contours of tooth 33' and a portion of neighboring teeth 32' and 34' corresponding to tooth 33 and teeth 32 and 34, respectively. The virtual image displays the image of the teeth, which will be captured by the camera when the bracket will be in its proper position.

Figure 4C:
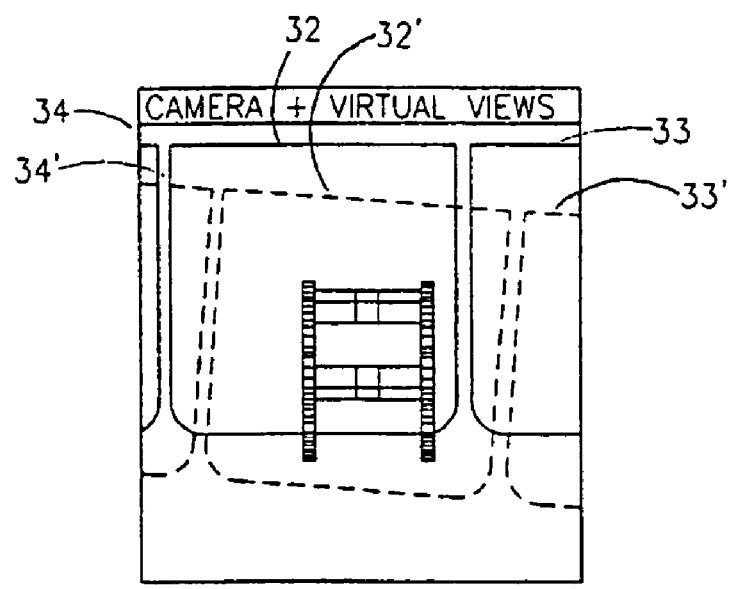

Superimposition of the two views can be seen in FIG. 4C. To attain a proper position, the bracket-positioning device has to be manipulated so as to cause the real image to tilt until matching the real life virtual images.

Figure 5A:
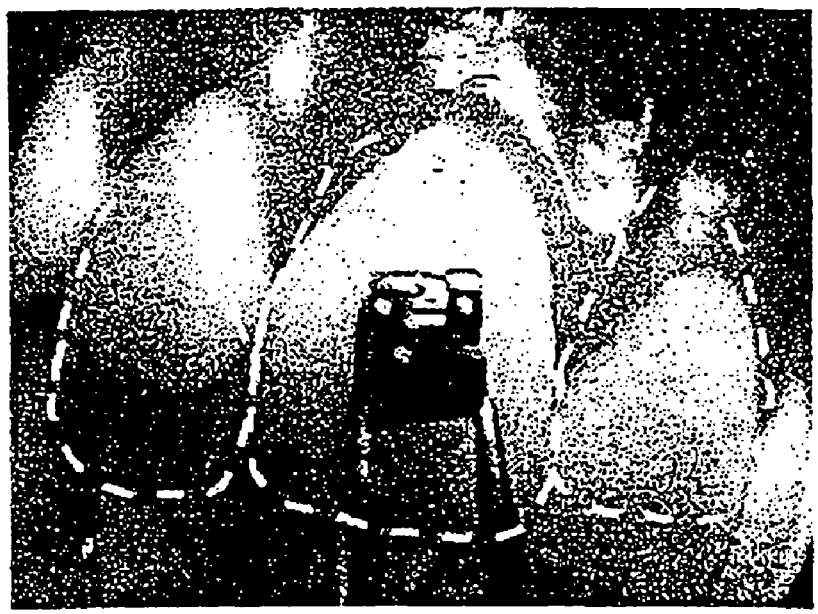
Figure 5B:
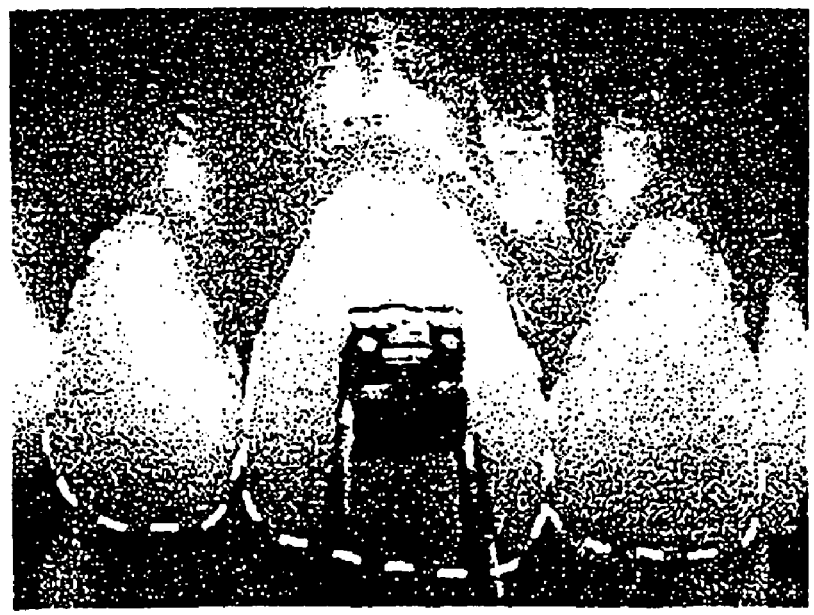

FIG. 5 shows a picture of an image as captured by a camera mounted on the bracket positioning device, superimposed with a virtual image in the form of lines tracing the boundaries of the teeth. FIG. 5A shows a state where the bracket is in a position other than the proper position. By repositioning the bracket until the virtual image matches the boundaries of the teeth, a proper positioning of the bracket is attained.

Figure 6:
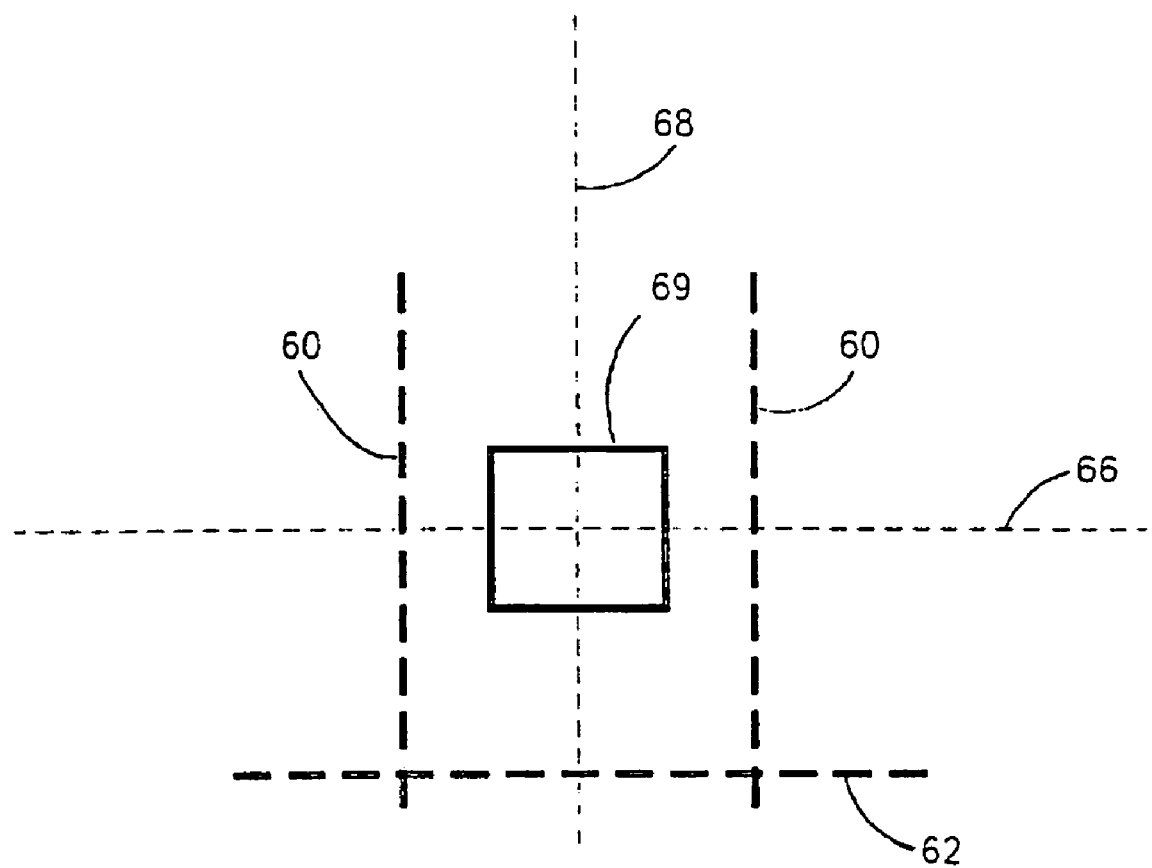
FIG. 6 illustrates another embodiment of displaying information regarding the proper position, where rather than lines tracing the boundaries of teeth, displayed are reference lines defining the teeth boundaries.

FIG. 6 shows an alternative manner of displaying information regarding proper position. In this case, rather than displaying the boundaries of the teeth, reference lines 60, 62 and 64 are provided which define the extreme boundaries of the teeth. In addition, optionally, bracket positioning lines 66 and 68 may also be displayed to ensure that the bracket (represented schematically by rectangle 69) is properly fitted on the bracket placer device; in a proper placement, bracket 69 will have its center on the crossing point between lines 66 and 68.

Figure 7A:
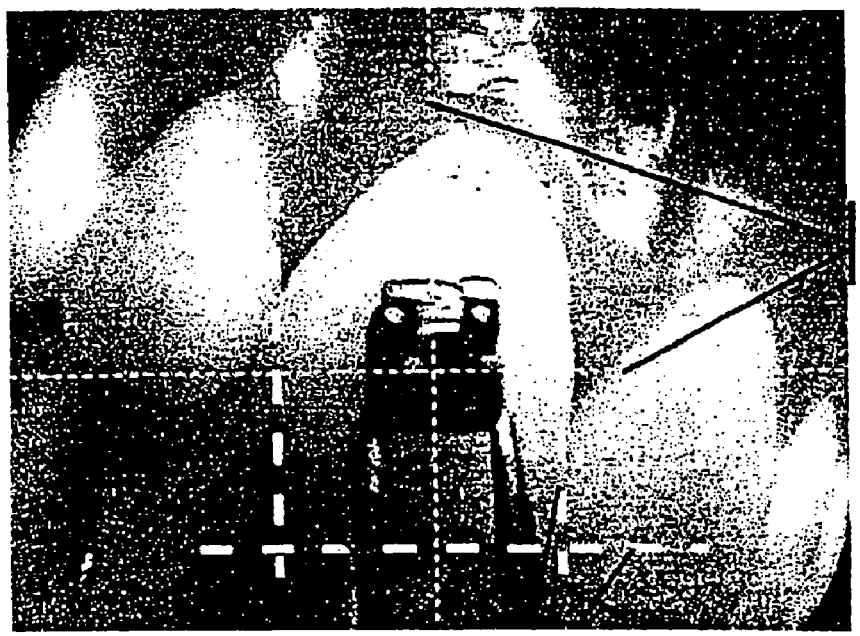
FIG. 7 shows an image similar to FIG. 5 where in this case, rather than displaying a virtual image in the form of lines tracing the boundaries of the teeth information on proper position is displayed in the manner illustrated in FIG. 6.
Figure 7B:
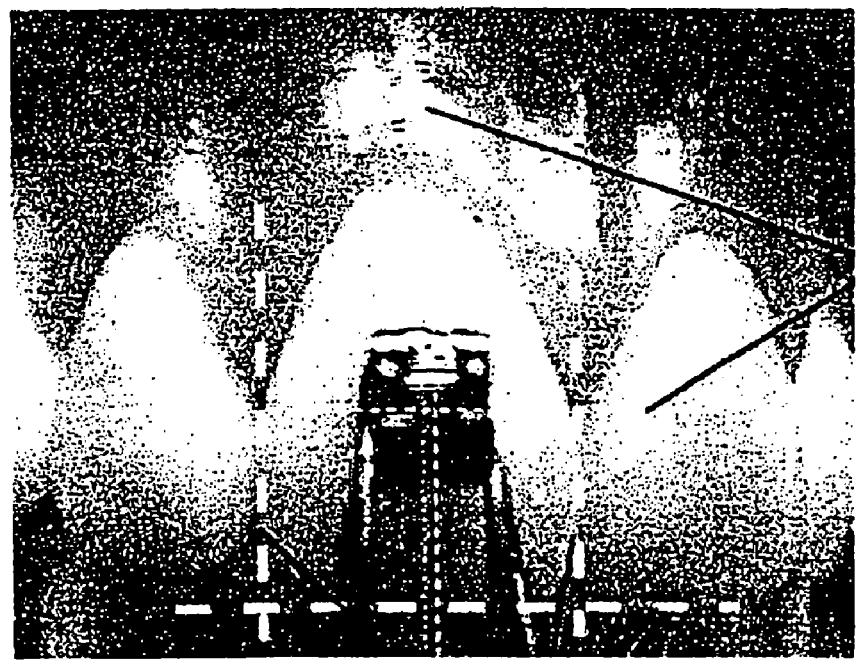

FIG. 7 shows the manner of obtaining proper positioning of a bracket in an analogous manner to that shown in FIG. 5 with FIG. 7A showing a state in which the bracket is in a position other than the proper position and FIG. 7B shows the state after changing position to reach a proper position of the bracket with the reference lines serving as guidelines.

Figure 8:
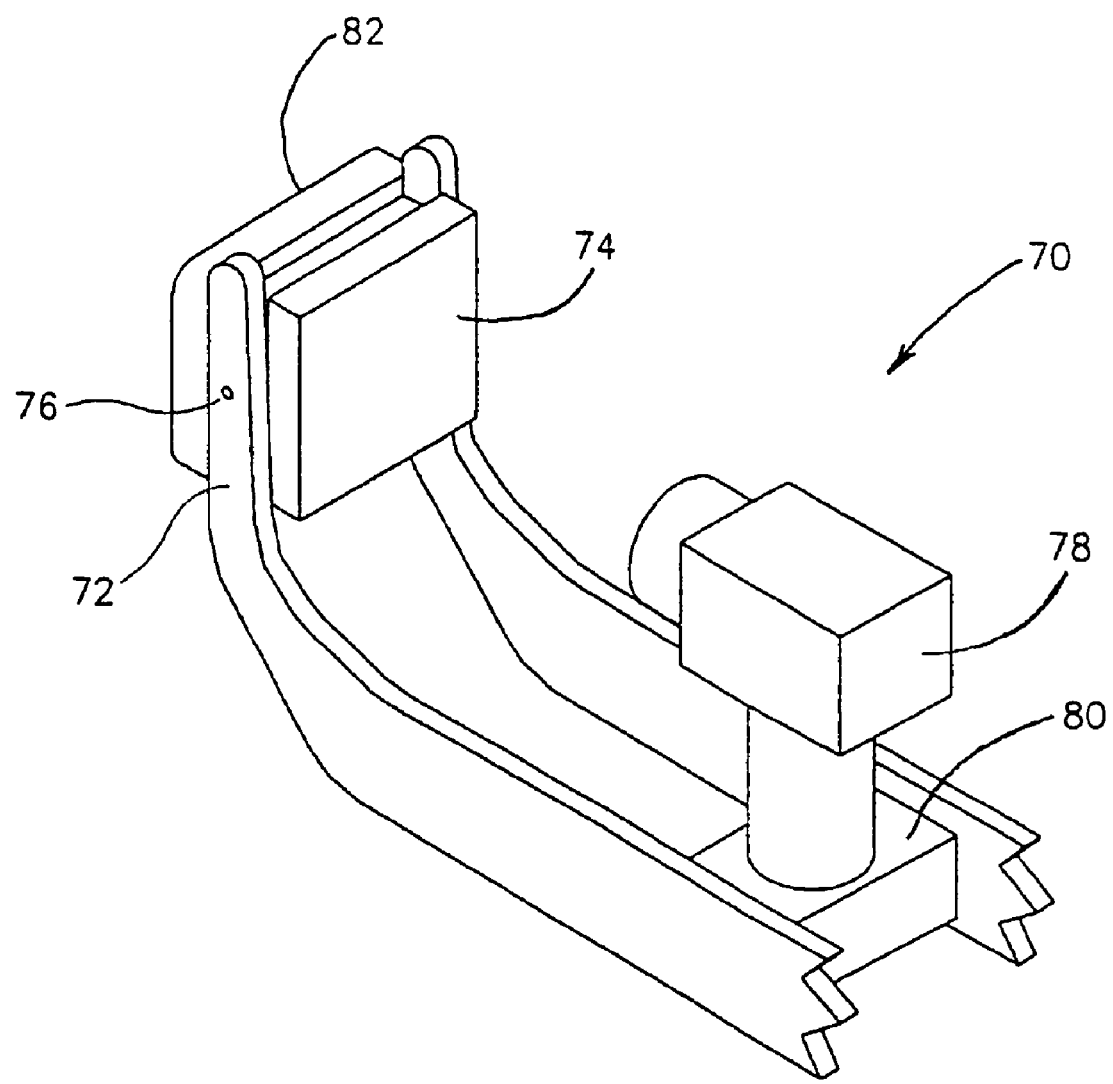
FIG. 8 shows a marking device in accordance with an embodiment of the invention.

FIG. 8 shows a marking device 70 in accordance with an embodiment of the invention. Device 70 has a pair of gripping members 72 holding between them a marking member 74 fixed in position by means of pin 76. Device 70 further comprises a video camera 78, mounted on a mount 80 integral with members 72, being positioned and having a field of view such that it fuels marker member 74 essentially the center of its field of view. Marking member 74 has the general shape representing that of a bracket and has a tooth engaging surface 82, which is capable of stamping a mark on a tooth which swill thereafter serve as a Guidance for proper positioning and subsequent fixing of a bracket. Positioning of member 74 thus to achieve a proper position may be carried out similarly as described above in reference to FIGS. 4–7.

The invention claimed is:

1. A method for positioning and fixing an orthodontic element on a surface, comprising:
   a. mounting the element on a positioning device having an image acquisition unit mounted thereon such that said element is in the field of view of said unit;
   b. bringing the element into proximity of the surface while continuously capturing an image of the element and of the surface;
   c. transmitting the image or its representation to a display for displaying a real-life image of the captured image or representation together with indicators providing guidance information on intended position of the orthodontic element on the surface;
   d. positioning the element on a surface according to said indicators such that the element's position coincides with the intended position; and
   e. fixing the element onto the surface.

2. A method according to claim 1, wherein said indicators comprise a virtual image of at least one surface, and proper position is achieved by matching the real-life image with the virtual image.

3. A method according to claim 2, wherein said element is fixed such that it is in a fixed position of the acquired image.

4. A method according to claim 2, wherein the virtual image comprises boundaries of the surface, the orthodontic element or of both.

5. A method according to claim 4, wherein the virtual image comprises a virtual image of the orthodontic element superimposed on said real-life image indicating the correct position and orientation of the orthodontic element on a surface.

6. A method according to claim 4, wherein
   the virtual image is a virtual image of at least one surface,
   the image of the orthodontic element is displayed at a fixed position and orientation of the display, and
   positioning the element on the surface is achieved by manipulating the element such that the at least one surface of the image overlaps the at least one surface of the virtual image.

7. A method according to claim 1, wherein said element is an orthodontic bracket.

8. A method for positioning and fixing an orthodontic element on
   a surface, comprising:
      a. mounting the element on a positioning device having an image acquisition unit mounted thereon such that said element is in the field of view of said unit;
      b. bringing the element into proximity of said surface while continuously monitoring the element by said image acquisition unit which captures an image of the element and its surrounding and transmits this image to a screen:
      c. displaying on the screen
         i. said image
         ii. guidance information relating to a proper position of the element on said surface;

d. in case of discrepancy between actual position of said element, being the position of the element viewed on the screen, and said proper position, correcting the actual position to match said proper position; and
e. fixing said element on said surface.

9. A method according to claim 8, wherein the position of the element is such so that the element appears in the center of the image displayed on the screen.

10. A method for comparing between an orthodontic element's actual position on a surface and a proper position, the method comprising:
   a. monitoring the element, the surface or both once the element and the surface are proximal to one another by an image acquisition unit mounted on a positioning device that can hold the element and position it on a surface, the image acquisition unit transmits an image to a screen that displays said image;
   b. displaying information on said screen regarding proper position of said element on the surface in a manner that allows to compare between the actual and the proper position.

11. A method according to claim 10 wherein the information regarding the proper position of the element comprises a virtual image of the surface.

12. A method according to claim 11, wherein the virtual image comprises lines tracing boundaries of the surface.

13. A method according to claim 12, comprising superimposing the virtual image with a real image captured by the image acquisition unit displayed on the screen.

14. A method according to claim 11, comprising superimposing the virtual image with a real image captured by the image acquisition unit displayed on the screen.

15. A method according to claim 10, wherein said element is an orthodontic bracket.

16. A method according to claim 10, wherein said element is held on by said device in a fixed, predetermined position.

17. A method according to claim 16, wherein the position of the element is such so that the element appears in the center of the image displayed on the screen.

\* \* \* \* \*